US012788321B2

(12) United States Patent
Gur Arieh et al.

(10) Patent No.: US 12,788,321 B2
(45) Date of Patent: Nov. 10, 2026

(54) PRESS-FIT LOCKABLE HOUSING CONFIGURED TO ATTACH TO FLEXIBLE MATERIALS

(71) Applicant: LittleOne Care Ltd., Tel Aviv (IL)

(72) Inventors: Shauli Gur Arieh, Jerusalem (IL); Yosi Sabbag, Holon (IL); Amram Meoded, Sha'arei Tikva (IL); Evgeni Machavariani, Rishon LeTsiyon (IL)

(73) Assignee: LittleOne Care Ltd., Tel Aviv (IL)

( * ) Notice: Subject to any disclaimer, the term of this patent is extended or adjusted under 35 U.S.C. 154(b) by 770 days.

(21) Appl. No.: 18/326,257

(22) Filed: May 31, 2023

(65) Prior Publication Data

US 2024/0398343 A1 Dec. 5, 2024

(51) Int. Cl.
*H05K 5/00* (2025.01)
*A61B 5/00* (2006.01)

(52) U.S. Cl.
CPC .................................. *A61B 5/6804* (2013.01)

(58) Field of Classification Search
None
See application file for complete search history.

(56) References Cited

U.S. PATENT DOCUMENTS

| | | | |
|---|---|---|---|
| 9,345,433 B1 | 5/2016 | Shinozuka et al. | |
| 9,750,456 B2 | 9/2017 | Vaitaitis | |
| 10,109,963 B2 * | 10/2018 | Komoto | A41D 1/002 |
| 11,812,842 B2 * | 11/2023 | Perkins | H04L 9/0825 |
| 12,070,059 B2 * | 8/2024 | Patel | B65D 81/22 |
| 2017/0279230 A1 * | 9/2017 | Komoto | H01R 13/2442 |
| 2019/0053757 A1 | 2/2019 | Cooper et al. | |
| 2022/0004837 A1 * | 1/2022 | Perkins | G06F 3/02 |

* cited by examiner

*Primary Examiner* — Imani N Hayman
*Assistant Examiner* — Rashen E Morrison
(74) *Attorney, Agent, or Firm* — Intrinsic Law Corp.

(57) ABSTRACT

An apparatus comprises a housing and a ring. The housing includes a front, a back, and a side, the side having a slot that extends long a perimeter of the housing, the housing having multiple corners. The ring has a variable-width wall as measured with respect to a radius of the ring, the variable-width wall defining multiple sets of internal surfaces, each set configured to be aligned with the corners of the housing at different rotational positions of the ring relative to the housing, each set of internal surfaces defining a respective gap between each housing corner and a respective set of internal surfaces when the corners are aligned with the respective set of internal surfaces. When a flexible material is located between the housing and the ring, a press-fit lock is formed when the ring is rotated relative to the housing to attach the apparatus to the flexible material.

14 Claims, 17 Drawing Sheets

PRESS-FIT LOCKABLE HOUSING CONFIGURED TO ATTACH TO FLEXIBLE MATERIALS

TECHNICAL FIELD

This application relates generally to mechanical attachments.

BACKGROUND

Lockable housings and attachments are used in a variety of applications. For example, a lockable housing can be used to provide releasable access to an electronic device located in a portion of the lockable housing.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an apparatus comprising a housing having a front, a back, and a side, the side having a slot that extends long a perimeter of the housing, the housing having a plurality of corners; and a ring having a variable-width wall along a circumference of the ring, the variable-width wall measured with respect to a radius of the ring, the variable-width wall defining multiple sets of internal surfaces, each set of internal surfaces configured to be aligned with the corners of the housing at different rotational positions of the ring relative to the housing, each set of internal surfaces defined by a respective width of the variable-width wall to define a respective gap between each corner of the housing and a respective set of internal surfaces when the corners are aligned with the respective set of internal surfaces, wherein when a flexible material is located between the housing and the ring, the apparatus is configured to form a press-fit lock when the ring is rotated relative to the housing to attach the apparatus to the flexible material.

In one or more embodiments, the plurality of internal surfaces includes a first set of internal surfaces configured to define a first opening in the ring, the first opening larger than a bottom of the housing to allow the housing to be placed within or removed from the ring when the ring is in a first rotational position relative to the housing, the first opening including a first gap between each corner of the housing and the first set of internal surfaces when the ring is in the first rotational position. In one or more embodiments, the plurality of internal surfaces includes a second set of internal surfaces configured to define a second opening in the ring, the second opening including a second gap between each corner of the housing and the second set of internal surfaces when the ring is in a second rotational position relative to the housing, the second gap smaller than the first gap, wherein the apparatus is configured to transition to a locked state when the flexible material is located between the housing and the ring including in the second gap to form the press-fit lock.

In one or more embodiments, the locked state is a first locked state, the press-fit lock is a first press-fit lock, the flexible material is a thick flexible material, and the plurality of internal surfaces includes a third set of internal surfaces configured to define a third opening in the ring, the third opening including a third gap between each corner of the housing and the third set of internal surfaces when the ring is in a third rotational position relative to the housing, the third gap smaller than the second gap, wherein the apparatus is configured to transition to a second locked state when a thin flexible material is located between the housing and the ring including in the third gap to form a second press-fit lock, the thin flexible material being thinner than the thick flexible material. In one or more embodiments, a gasket is located on the side of the housing, the gasket configured to compress when the apparatus is in the first locked state and/or in the second locked state to increase a range of thicknesses of the thick flexible material and/or of the thin flexible material, respectively, that can form the first press-fit lock and/or the second press-fit lock, respectively. In one or more embodiments, the gasket is located in a slot defined by first and second flanges, the first and second flanges overhanging the second and third internal surfaces when the ring is in the second and third rotational positions, respectively, relative to the housing, the first and second flanges restricting a movement of the housing relative to the ring in a direction orthogonal to a plane of the ring. In one or more embodiments, the first flange is larger than the first opening of the ring to mechanically engage the variable-width wall when the ring is in the first rotational position relative to the housing.

In one or more embodiments, the housing has rounded corners, and each set of internal surfaces is rounded to conform to the rounded corners of the housing. In one or more embodiments, each of the third set of internal surfaces is at least partially defined by a respective ridge that is configured to physically contact the respective corner of the housing to prevent the ring from being rotated in a first direction beyond the third rotational position. In one or more embodiments, when the ring is in the first rotational position, the respective ridge is configured to physically contact the respective corner of the housing when the ring is rotated in a second direction, opposite to the first direction, such that the ring can only be rotated in the first direction to transition to the second and third rotational positions.

In one or more embodiments, the respective ridge is a first respective ridge, and each of the third set of internal surfaces is at least partially defined by a respective second ridge that is configured to form a respective second-ridge gap between each corner of the housing and the respective second ridge when each corner is aligned with the respective second ridge, the respective second-ridge gap smaller than the second and third gaps to limit a relative rotation between the ring and the housing when the ring is in the second or third rotational position. In one or more embodiments, each of the second set of internal surfaces is at least partially defined by the respective second ridge and a respective third ridge, the respective third ridge configured to form a respective third-ridge gap between each corner of the housing and the respective third ridge when each corner is aligned with the respective third ridge, the respective third-ridge gap smaller than the second gap to limit the relative rotation between the ring and the housing when the ring is in the second rotational position.

In one or more embodiments, the front and back of the housing have four corners, each set of internal surfaces has four internal interfaces, and when the ring is oriented such that the first set of internal surfaces is symmetric with respect to a center line of the ring, the second and third sets of internal surfaces are angularly offset with respect to the center line.

In one or more embodiments, a first internal surface in the first set of internal surfaces is defined by a first length that is measured with respect to the center line, a second internal surface in the first set of internal surfaces is defined by a second length that is measured with respect to the center line, the first length is larger than the second length, and the first set of internal surfaces has a mirror-image symmetry in the ring.

In one or more embodiments, the ring includes a flange along a circumference of the ring.

Another aspect of the invention is directed to an apparatus comprising a housing having a front, a back, and a side, the side having a slot that extends long a perimeter of the housing, the housing having a plurality of corners; one or more electronic devices located in the housing; and a ring having a variable-width wall along a circumference of the ring, the variable-width wall measured with respect to a radius of the ring, the variable-width wall defining multiple sets of internal surfaces, each set of internal surfaces configured to be aligned with the corners of the housing at different rotational positions of the ring relative to the housing, each set of internal surfaces defined by a respective width of the variable-width wall to define a respective gap between each corner of the housing and a respective set of internal surfaces when the corners are aligned with the respective set of internal surfaces, wherein when a flexible material is located between the housing and the ring, the apparatus is configured to form a press-fit lock when the ring is rotated relative to the housing to attach the apparatus to the flexible material.

In one or more embodiments, the plurality of internal surfaces includes a first set of internal surfaces configured to define a first opening in the ring, the first opening larger than a bottom of the housing to allow the housing to be placed within or removed from the ring when the ring is in a first rotational position relative to the housing, the first opening including a first gap between each corner of the housing and the first set of internal surfaces when the ring is in the first rotational position. In one or more embodiments, the plurality of internal surfaces includes a second set of internal surfaces configured to define a second opening in the ring, the second opening including a second gap between each corner of the housing and the second set of internal surfaces when the ring is in a second rotational position relative to the housing, the second gap smaller than the first gap, wherein the apparatus is configured to transition to the locked state when the flexible material is located between the housing and the ring including in the second gap to form the press-fit lock.

In one or more embodiments, the locked state is a first locked state, the press-fit lock is a first press-fit lock, the flexible material is a thick flexible material, and the plurality of internal surfaces includes a third set of internal surfaces configured to define a third opening in the ring, the third opening including a third gap between each corner of the housing and the third set of internal surfaces when the ring is in a third rotational position relative to the housing, the third gap smaller than the second gap, wherein the apparatus is configured to transition to a second locked state when a thin flexible material is located between the housing and the ring including in the third gap to form a second press-fit lock, the thin flexible material being thinner than the thick flexible material. In one or more embodiments, a permanent magnet is attached to or embedded in the ring; the one or more electronic devices includes a magnetometer and a processor circuit in electrical communication with the magnetometer, the magnetometer measures a magnetic field produced by the permanent magnet, the magnetometer and the permanent magnet are positioned such that a relative position of the magnetometer with respect to the permanent magnet changes when the ring is in the second or third rotational position compared to when the ring is in the first rotational position, one or more characteristics of the magnetic field measured by the magnetometer is different when the ring is in the second or third rotational position compared to when the ring is in the first rotational position, and the processor circuit is configured to produce an output signal when the one or more characteristics of the magnetic field indicate(s) that the ring is in the first rotational position.

BRIEF DESCRIPTION OF THE DRAWINGS

For a fuller understanding of the nature and advantages of the concepts disclosed herein, reference is made to the detailed description of preferred embodiments and the accompanying drawings.

DETAILED DESCRIPTION

A lockable apparatus configured to form a press-fit lock with a flexible material, such as an article of clothing, is disclosed. The apparatus includes a housing and a ring. The ring includes a variable-width wall along a circumference of the ring. The variable-width wall defines multiple sets of internal surfaces. Each set of internal surfaces is configured to be aligned with some or all of the corners of the housing at different rotational positions of the ring relative to the housing (or vice versa). Each set of internal surfaces is defined by a respective width of the variable-width wall to define a respective gap between the housing corners and a corresponding set of internal surfaces when the housing corners are aligned with that set of internal surfaces. The gap defined by at least one set of the internal surfaces is configured to cause the housing corners to mechanically engage the at least one set of the internal surfaces to form a press-fit lock when the flexible material is located in the gap.

Figure 1:
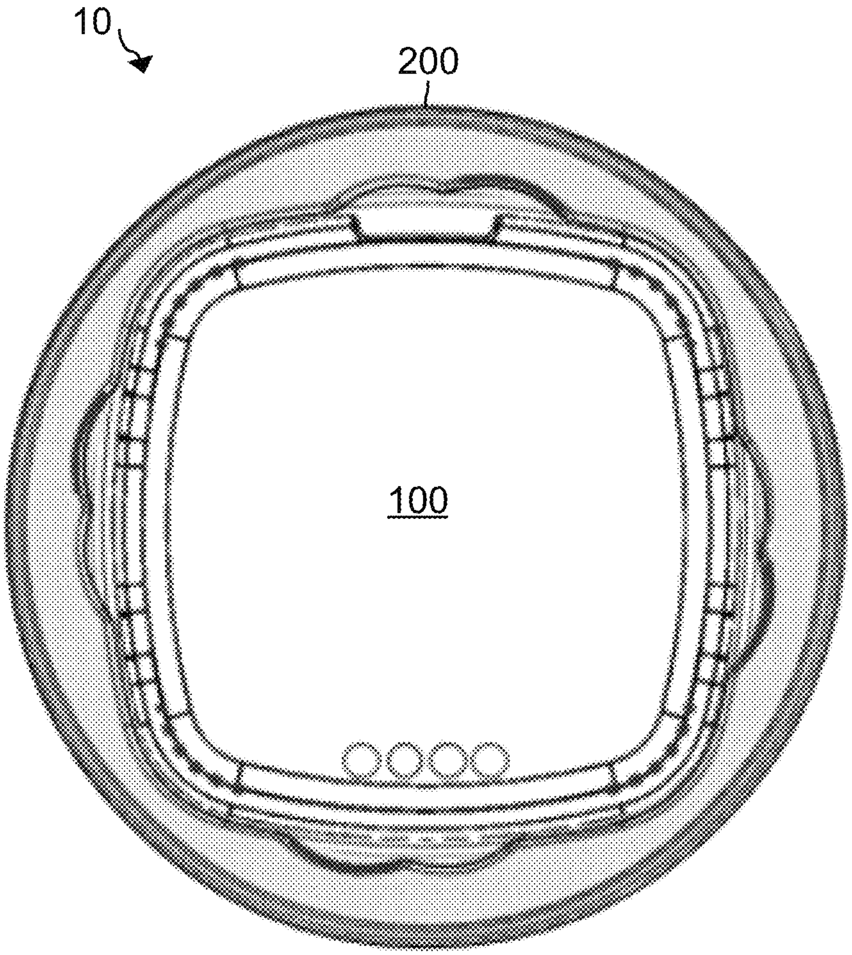
FIG. 1 is a top view of a configurable apparatus in a releasable configuration according to an embodiment.

FIG. 1 is a top view of a configurable apparatus 10 according to an embodiment. The apparatus 10 includes a housing 100 and a ring 200. The housing 100 and ring 200 are separate mechanical parts that are configured to releasably mechanically engage each other to form a friction-fit or press-fit lock to attach the apparatus 10 to a flexible material such as a fabric (e.g., clothing). The apparatus 10 can also be secured to other flexible materials such as paper, thin sheets of plastic, and/or other flexible materials. A specific example of a flexible material is fabric, such as cotton or polyester, used in baby clothing. The flexible material can have a thickness, for example, in the range of about 0.5 mm to about 2 mm, including about 1 mm, about 1.5 mm, and any value or range between any two of the foregoing values.

The apparatus 10 is illustrated in a releasable configuration in which the housing 100 and the ring 200 can be separated from each other (e.g., when detaching the apparatus 10 from a fabric material) or in which the housing 100 and the ring 200 can mechanically engage each other (e.g., when attaching the apparatus 10 to a fabric material). The housing 100 can rotate with respect to the ring 200 to transition the apparatus 10 into one or more locked configurations. Additionally or alternatively, the ring 200 can rotate with respect to the housing 100 to transition the apparatus 10 into one or more locked configurations. Thus, relative rotational movement of the ring 200 with respect to the housing 100 (or vice versa) transitions the apparatus 10 into one or more locked configurations.

In one embodiment, the housing 100 includes an electronics device 102 that can be releasably secured to clothing using the apparatus 10. The electronics device can include one or more sensors, one or more processor circuits, computer (e.g., memory circuits), electronic peripherals, and/or communications circuitry. In a specific embodiment, the electronics device include one or more sensors for monitoring a baby or an adult (in general, a human) and associated communications circuitry.

The housing 100 has corners 104. The corners 104 are defined by a square shape of the top 110 and bottom 120 of the housing 100. The top and bottom 110, 120 can alternately be referred as to the front and back 110, 120, respectively. The square shape can have, for example, a length and width of about 30 mm to about 50 mm, including about 35 mm, about 40 mm, about 45 mm, and any range or value between any two of the foregoing dimensions. In other embodiments, the top 110 and bottom 120 can have another shape such as a rectangle or another regular geometric shape. In other embodiments, the top 110 and bottom 120 can have an irregular geometric shape. The corners 104 are preferably rounded and/or curved. As used herein, "about" means plus or minus 10% of the relevant value.

The thickness or depth of the housing 100, for example, can be about 8 mm to about 13 mm, including about 9 mm, about 10 mm, 11 mm, about 12 mm, and any range or value between any two of the foregoing dimensions.

Figure 2:
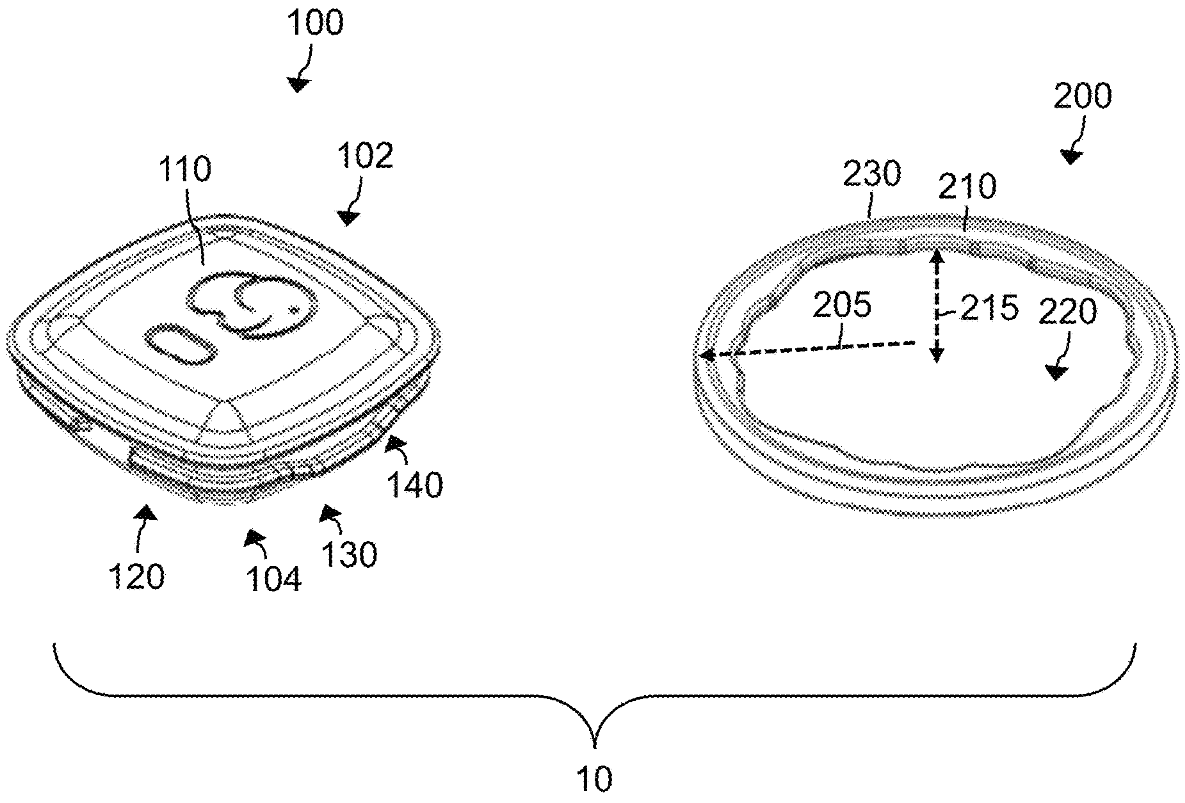
FIG. 2 is a perspective view of the apparatus illustrated in FIG. 1 in an unassembled configuration.

FIG. 2 is a perspective view of the apparatus 10 in an unassembled configuration. The housing 100 includes a top 110, a bottom 120, and a side 130. The side 130 is located between the top 110 and bottom 120 and extends along a perimeter of the housing 100. A slot 140 is defined in the side 130 of the housing 100. The slot 140 preferably extends along the perimeter of the housing 100.

The ring 200 is formed by a wall 210 having a variable width. The variable-width wall 210 defines a hole or opening 220 that has a variable width. The hole 200 is wider where the wall 210 is narrower. Conversely, the hole 220 is narrower where the wall 210 is wider. The width of the wall 210 and hole 220 are measured with respect to a radius 205 of the ring 200. The wall 210 has a thickness, as measured with respect to an axis 215 that is orthogonal to the radius and to the plane of the ring 200, that is smaller than a corresponding height of the slot 140 such that the wall 210 can fit into the slot 140.

The ring can have a diameter, for example, of about 45 mm to about 55 mm, including about 47 mm, about 49 mm, about 51 mm, about 53 mm, and any range or value between any two of the foregoing dimensions.

A flange 230 can be located along the perimeter of the ring 200. The flange 230 can have a height, for example, of about 2 mm to about 4 mm including about 2.5 mm, about 3 mm, about 3.5 mm, and any range or value between any two of the foregoing dimensions. The flange 230 can provide mechanical strength and/or mechanical support for the ring 200. Additionally or alternatively, the flange 230 can be used to grip/hold the apparatus 10.

Figure 3:
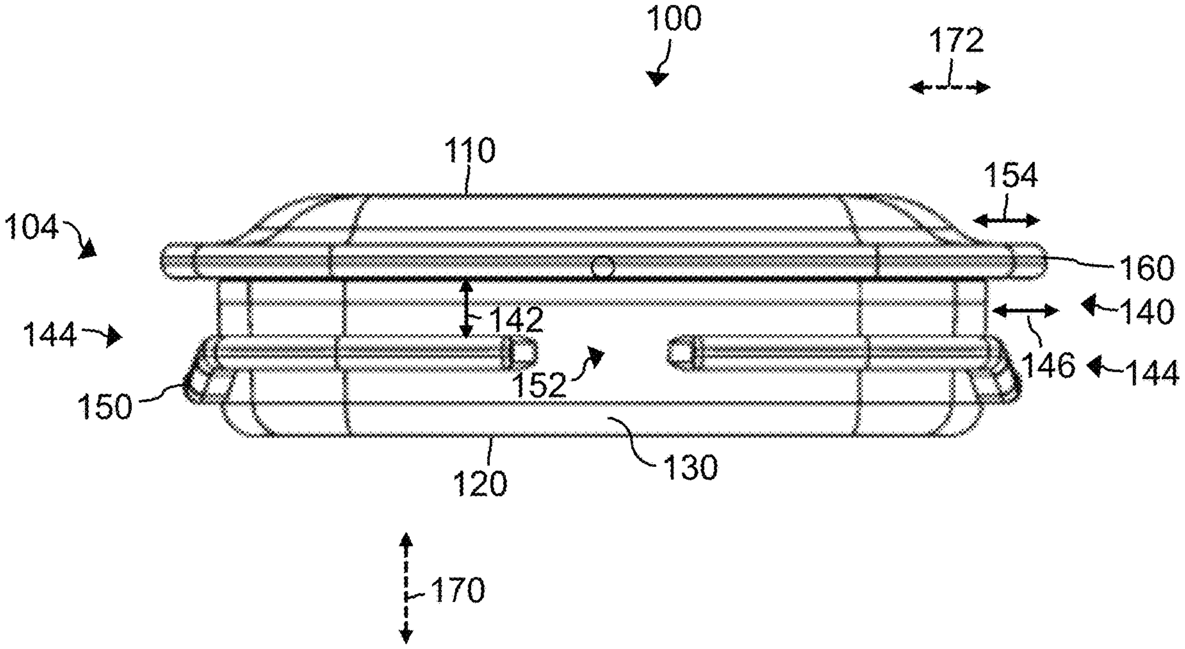
FIG. 3 is a side view of the housing illustrated in FIG. 1.

FIG. 3 is a side view of the housing 100 to further illustrate the side 130 of the housing 100.

The side 130 is preferably curved at the rounded corners 104 of the housing 100.

The slot 140 is defined by a lower flange 150 and an upper flange 160. The distance between the lower and upper flanges 150, 160 defines the height 142 of the slot 140. The height 142 of the slot 140 can vary along the perimeter of the housing 100. For example, the height 142 of the slot 140 can increase, such as at locations 144, for example to make it easier to mechanically engage and disengage the housing 100 and the ring 200 (e.g., the slot 140 and the wall 210, respectively). Locations 144 can be on opposite sides of the housing 100. Additionally or alternatively, one or more breaks 152 can be defined in the lower flange 150. The break(s) 152 can allow access to mechanically engage and disengage the housing 100 and the ring 200 (e.g., the slot 140 and the wall 210, respectively). The break(s) 152 can also be used to define an orientation of the housing 100 (and of the apparatus 10), for example to ensure that users place the apparatus 10 in the correct orientation in a dock or charging station.

The height 142 can be measured with respect to an axis 170 that is orthogonal to the top and bottom 110, 120 surfaces and that is parallel to axis 215 when the apparatus

10 is in the releasable configuration (FIG. 1). In another embodiment, the height 142 of the slot 140 can be the same or constant (or substantially the same or constant) along the sides 130 of the housing 100.

The width 154 of the lower and upper flanges 150, 160 defines a depth 146 of the slot 140. The width 154 and depth 146 can be measured with respect to an axis 172 that is orthogonal to axis 170 and parallel to the top and bottom 110, 120 surfaces. Axis 172 is parallel to the radius 205 when the apparatus 10 is in the releasable configuration (FIG. 1).

Figure 4:
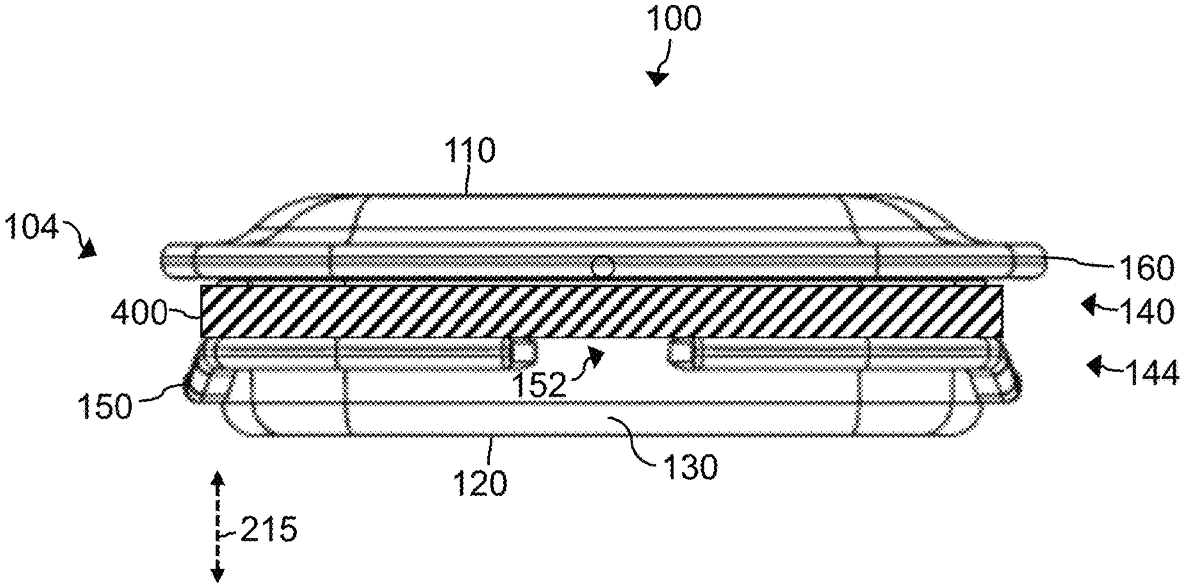
FIG. 4 is a side view of the housing according to another embodiment.

In some embodiments, a gasket 400 is located in and extends along the slot 140, as illustrated in FIG. 4. The gasket 400 can be compressed by the wall 210 of the ring 200 and any flexible material (e.g., clothing) between the wall and the ring 200, which allows the depth 146 of the slot 140 to vary. The variable depth 146 can allow the apparatus 10 to be secured to flexible materials having a range of thicknesses.

Figure 5:
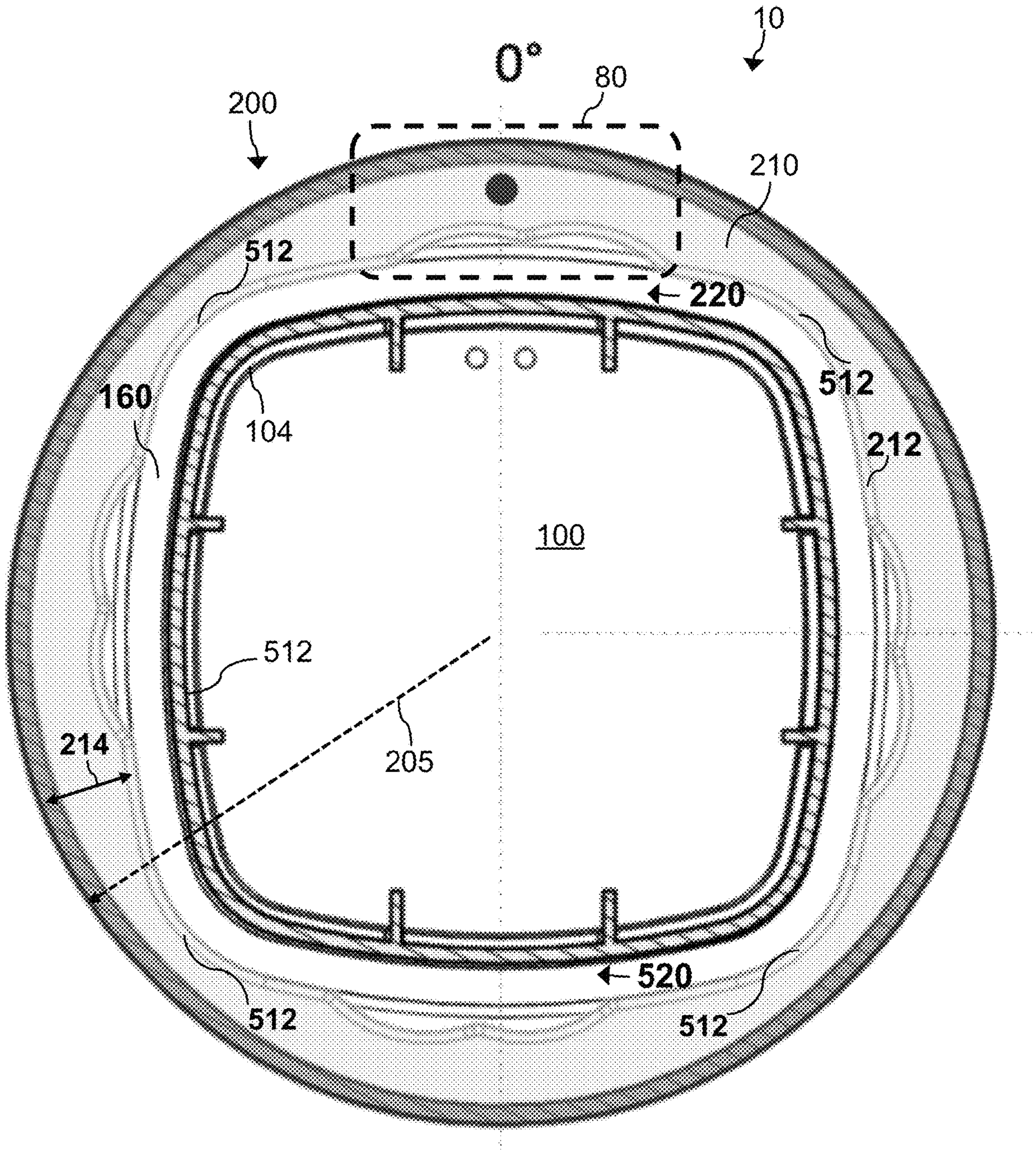
FIG. 5 is a bottom view of the apparatus illustrated in FIG. 1 to illustrated a first rotational position of the ring relative to the housing.

FIG. 5 is a bottom view of the apparatus 10 according to an embodiment.

The wall 210 of the ring 200 has multiple internal surfaces 212 that are generally oriented towards the hole 220. The internal surfaces 212 are defined by the variable width 214 of the wall 210. The width 214 of the wall 210 is measured with respect to an axis that is parallel to the radius 205 of the ring 200 at the corresponding position of the wall 210 to be measured.

The internal surfaces 212 can be divided into multiple sets that correspond to the respective rotational orientation of the housing 100 relative to the ring 200 (or vice versa). A first set of internal surfaces 512 on the wall 210 are configured to be aligned the corners 104 of the housing 100 in a first rotational position of the ring 200 relative to the housing 100. In the first rotation position, the apparatus 10 is in the releasable configuration as discussed with respect to FIG. 1. The first set of internal surfaces 512 are located at respective locations on the ring 200 where the width 214 is small. The small width 214 of the wall 210 increases the width of the hole 220 to provide clearance space for the ring 200 to be inserted over the housing 100 (or vice versa) and/or for the ring 200 to be removed from the housing 100 (or vice versa).

Thus, the first set of internal surfaces 512 define a first opening 520 to allow the housing 100 to be placed within the ring 200 (or vice versa) and/or to allow the housing 100 to be removed front the ring 200 (or vice versa). The first opening 520 represents an outline of a top-view of the housing 100 where the dimensions of the first opening 520 are larger than the bottom 120 and smaller than the top 110 of the housing 100.

When the ring 200 is in the first rotational position relative to the housing 100, at least a portion (e.g., some or all) of the upper flange 160 of the housing 100 is configured to extend beyond a first side of (e.g., behind) the wall 210 of the ring 200 to prevent the housing 100 from passing all the way through the ring 200.

Figure 6:
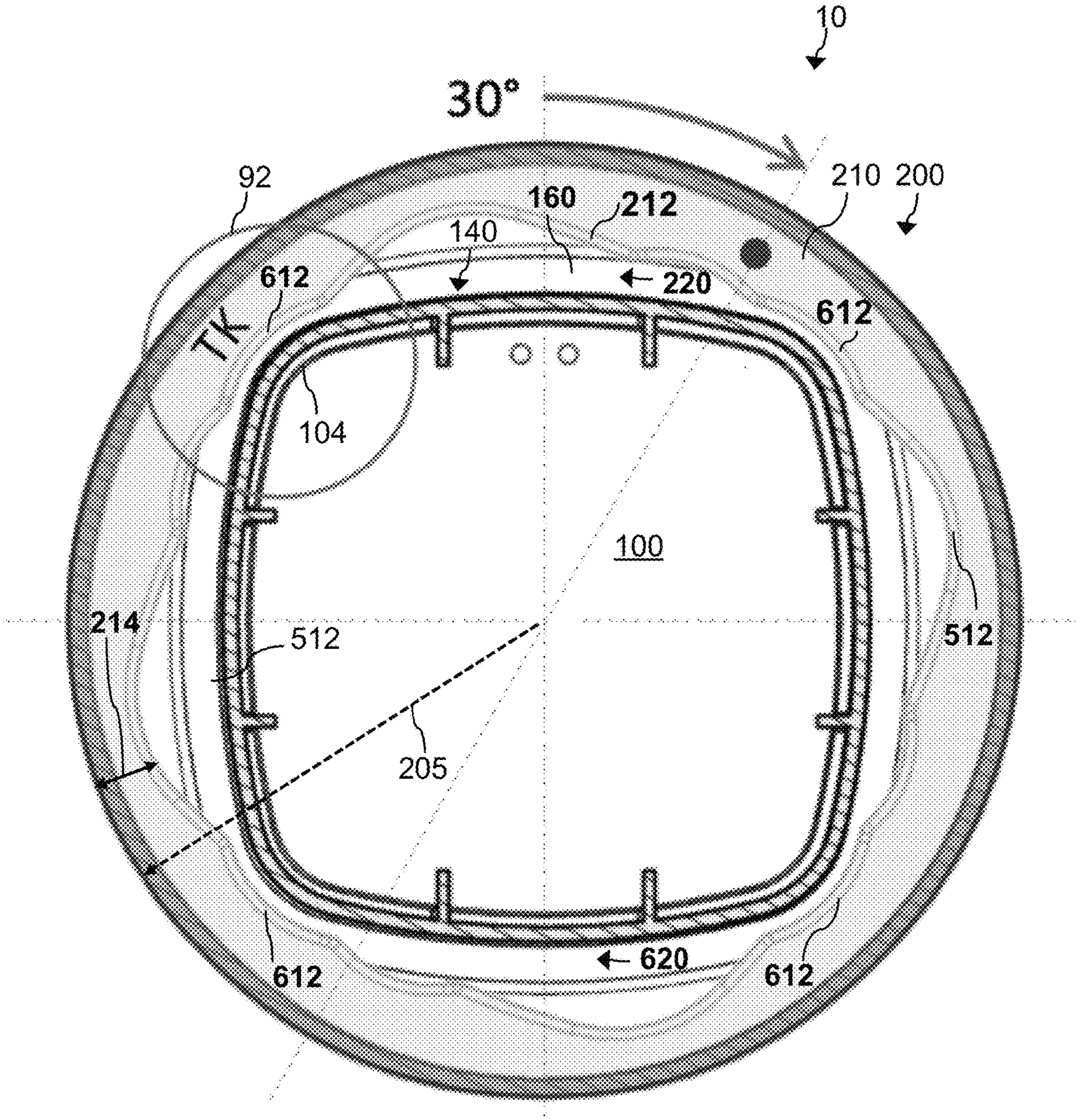
FIG. 6 is a bottom view of the apparatus illustrated in FIG. 1 to illustrated a second rotational position of the ring relative to the housing.

FIG. 6 is a bottom view of the apparatus 10 where the ring 200 is in a second rotational position relative to the housing 100 (or vice versa) according to an embodiment.

In the second rotational position, a second set of internal surfaces 612 on the wall 210 are configured to be aligned with the corners 104 of the housing 100. The second set of internal surfaces 612 are located at respective locations on the ring 200 where the width 214 is larger than at the locations of the first set of internal surfaces 512. The larger width 214 of the wall 210 decreases the width of the hole 220 at a second opening 620 of the ring 200. The second opening 620 is smaller than the first opening 520 to reduce the distance between the corners 104 and the wall 210 to form a friction-fit or press-fit lock when a relatively thick flexible material is located between the housing 100 and the ring 200. The second set of internal surfaces 612 can be referred as thick (TK) internal surfaces due to their ability to form a friction-fit or press-fit lock when a relatively thick flexible material is located between the housing 100 and the ring 200.

As seen from the bottom view, the apparatus 10 can transition from the first rotational position to the second rotational position by rotating the ring 200 counterclockwise relative to the housing 100 and/or by rotating the housing 100 clockwise relative to the ring 200. The second rotational position, for example, can be about 20 degrees to about 40 degrees, including about 25 degrees, about 30 degrees, about 35 degrees, and any range of value between any two of the foregoing angles from the first rotational position.

When the ring 200 is in the second rotational position relative to the housing 100, at least a portion (e.g., some or all) of the upper flange 160 of the housing 100 is configured to extend beyond a first side of (e.g., behind) the wall 210 of the ring 200 to prevent the housing 100 from passing all the way through the ring 200. A portion of the lower flange 150 can extend beyond a second side of (e.g., in front of) the wall 210 of the ring 200 to restrict movement of the housing 100 towards the first side of the wall 210. As such, lower and upper flanges 150, 160 can cause the wall 210 to maintain alignment with the slot 140.

Figure 7:
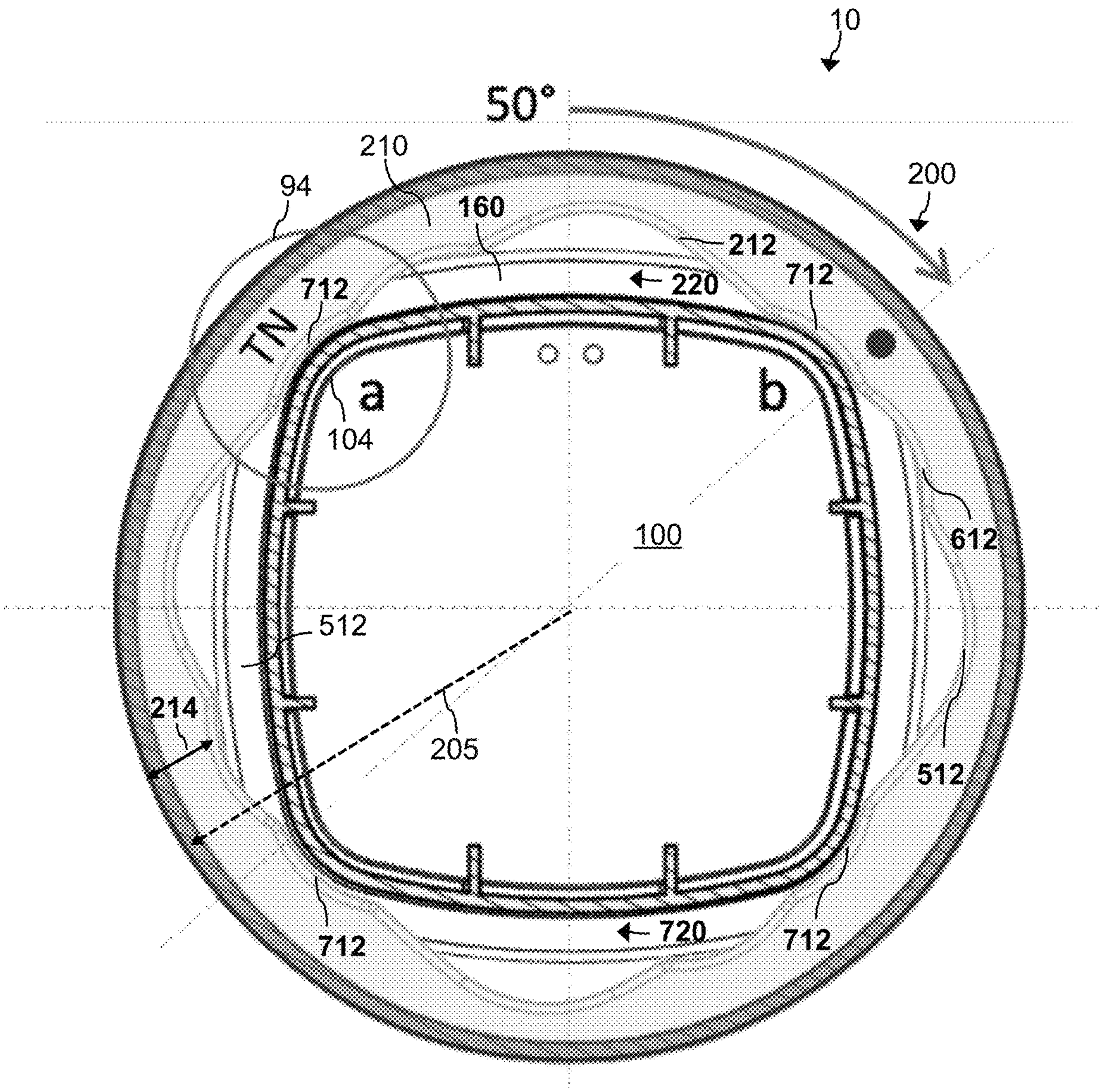
FIG. 7 is a bottom view of the apparatus illustrated in FIG. 1 to illustrated a third rotational position of the ring relative to the housing.

FIG. 7 is a bottom view of the apparatus 10 where the ring 200 is in a third rotational position relative to the housing 100 (or vice versa) according to an embodiment.

In the third rotational position, a third set of internal surfaces 712 on the wall 210 are configured to be aligned with the corners 104 of the housing 100. The third set of internal surfaces 712 are located at respective locations on the ring 200 where the width 214 is larger than at the locations of the second set of internal surfaces 612. The larger width 214 of the wall 210 decreases the width of the hole 220 at a third opening 720 of the ring 200 compared to the second opening 620 of the ring 200. The third opening 720 is smaller than the second opening 620 to reduce the distance between the corners 104 and the wall 210 to form a friction-fit or press-fit lock when a relatively thin flexible material is located between the housing 100 and the ring 200. The third set of internal surfaces 712 can be referred as thin (TN) internal surfaces due to their ability to form a friction-fit or press-fit lock when a relatively thin flexible material is located between the housing 100 and the ring 200.

The apparatus 10 can transition from the first rotational position to the second rotational position by rotating the ring 200 counterclockwise relative to the housing 100 and/or by rotating the housing 100 clockwise relative to the ring 200. The third rotational position can be, for example, about 40 degrees to about 60 degrees, including about 45 degrees, about 50 degrees, about 55 degrees, and any range of value between any two of the foregoing angles from the first rotational position. In addition, the third rotational position can be, for example, about 10 degrees to about 30 degrees, including about 15 degrees, about 20 degrees, about 25 degrees, and any range of value between any two of the foregoing angles from the second rotational position.

When the ring 200 is in the third rotational position relative to the housing 100, at least a portion (e.g., some or all) of the upper flange 160 of the housing 100 is configured to extend beyond a first side of (e.g., behind) the wall 210 of the ring 200 to prevent the housing 100 from passing all the way through the ring 200. A portion of the lower flange 150 can extend beyond a second side of (e.g., in front of) the wall 210 of the ring 200 to restrict movement of the housing 100 towards the first side of the wall 210. As such, lower and upper flanges 150, 160 can cause the wall 210 to maintain alignment with the slot 140.

In some embodiments, the second set of internal surfaces 612 or the third set of internal surfaces 712 can be optional in which case the apparatus 10 may only have one locked configuration. In other embodiments, one or more additional sets of internal surfaces 212 can be included which may provide the apparatus 10 with one or more additional locked configurations.

Figure 8:
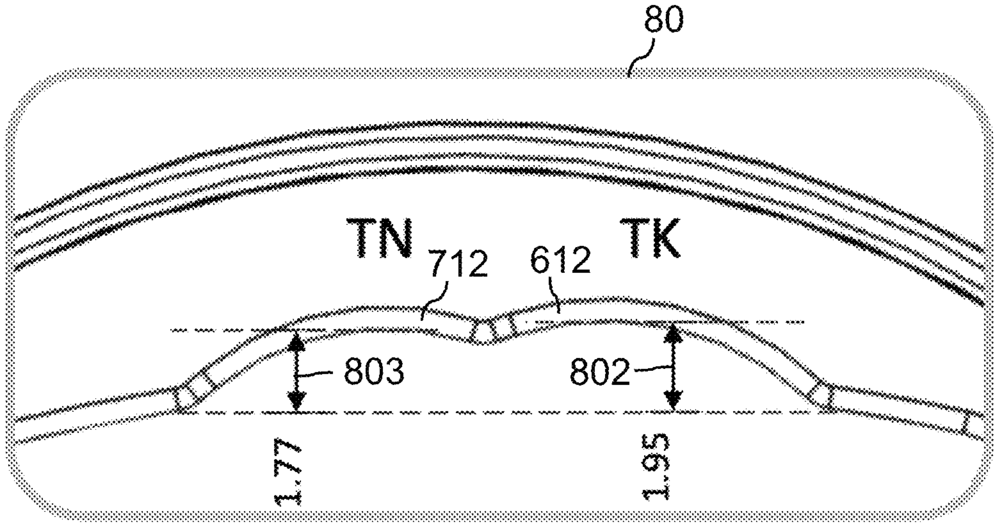
FIG. 8 is an enlarged view of region 80 in FIG. 5.

FIG. 8 is an enlarged view of region 80 in FIG. 5 to further illustrate the second and third internal surfaces 612, 712, respectively. The second and third internal surfaces 612, 712 are curved and define respective recesses 802, 803. Recess 802 is larger than recess 803. The larger size allows a thicker flexible material to fit in recess 802 compared to recess 803. Conversely, the smaller size allows a thinner flexible material to fit in recess 803 compared to recess 802. Example dimensions (in mm) are illustrated in FIG. 8, which are not intended to be limiting.

Figure 9A:
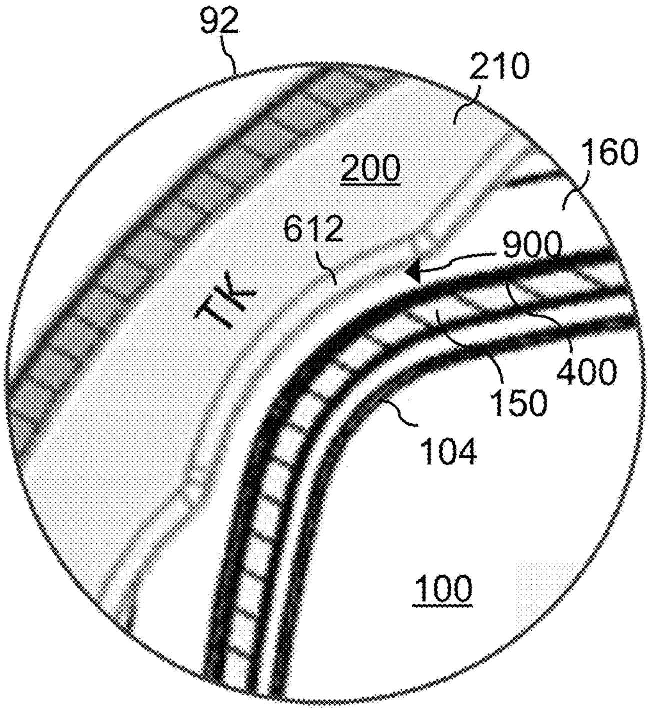
FIG. 9A is an enlarged view of region 92 in FIG. 6.

FIG. 9A is an enlarged view of region 92 in FIG. 6 to illustrate the gap 900 formed between the rounded corner 104 of the housing 100 and the second internal surface 612 when the ring 200 is in the second rotational position relative to the housing 100. It can be seen that the curvature of the second internal surface 612 is the same as (or is complementary to) the curvature of the rounded corner 104 of the housing 100 such that the gap 900 between the rounded corner 104 and the second internal surface 612 is uniform (or substantially uniform). In the illustrated embodiment, the gap 900 is between the second internal surface 612 and the gasket 400. In other embodiments that do not include a gasket, the gap 900 is between the second internal surface 612 and the side 130 of the housing 100 in the slot 140.

Figure 9B:
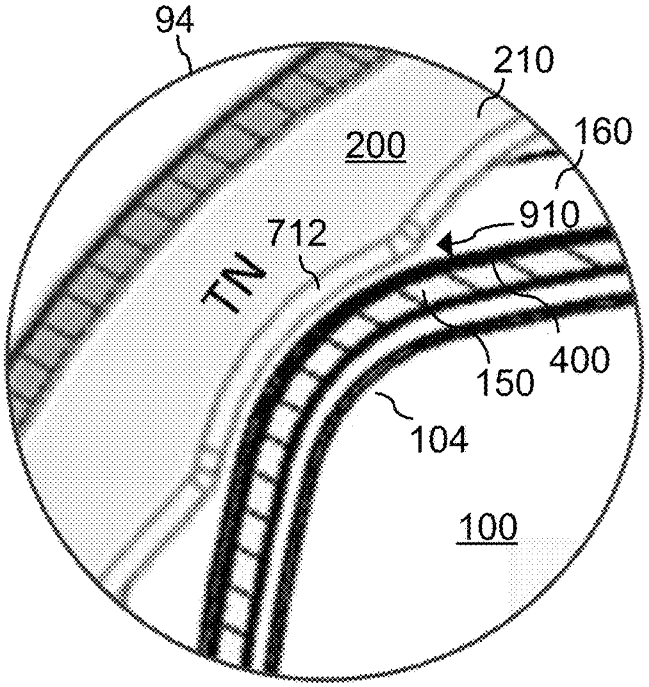
FIG. 9B is an enlarged view of region 94 in FIG. 7.

FIG. 9B is an enlarged view of region 94 in FIG. 7 to illustrate the gap 910 formed between the rounded corner 104 of the housing 100 and the third internal surface 712 when the ring 200 is in the third rotational position relative to the housing 100. It can be seen that the curvature of the third internal surface 612 is the same as (or is complementary to) the curvature of the rounded corner 104 of the housing 100 such that the gap 910 between the rounded corner 104 and the third internal surface 712 is uniform (or substantially uniform). In the illustrated embodiment, the gap 910 is between the third internal surface 712 and the gasket 400. In other embodiments that do not include a gasket, the gap 910 is between the third internal surface 712 and the side 130 of the housing 100 in the slot 140.

Gap 910 is configured to accommodate a relatively thin flexible material compared to gap 900. Gap 900 is configured to accommodate a relatively thick flexible material compared to gap 910. Gap 910 is smaller than gap 900.

Figure 10A:
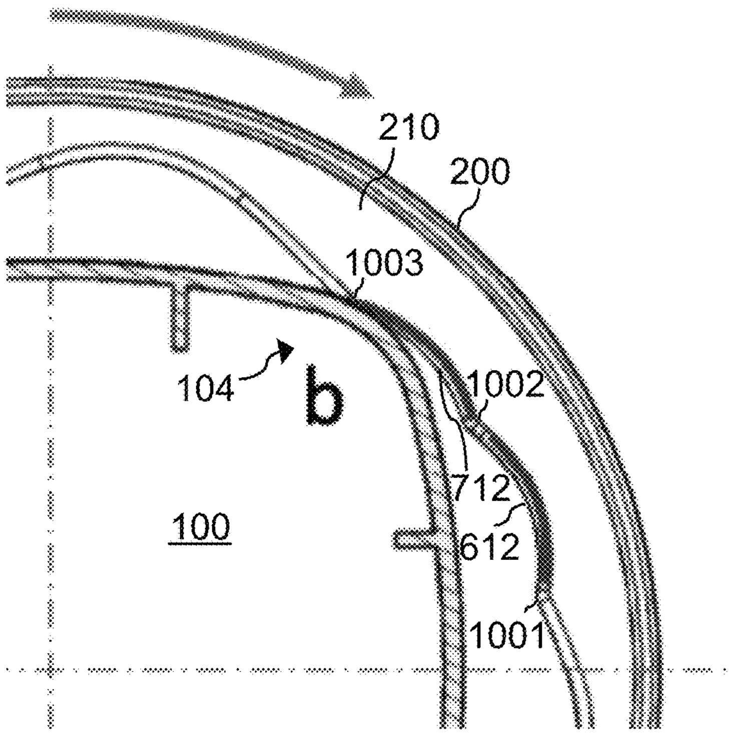
FIG. 10A is an enlarged view of the upper-right corner of the housing and a corresponding portion of the ring.

FIG. 10A is an enlarged view of the upper-right corner 104 of the housing 100 and a corresponding portion of the ring 200. The upper-right corner 104 corresponds to corner "b" in FIG. 7.

The second and third internal surfaces 612, 712 are defined by a respective pair of ridges. The second internal surface 612 is defined by and terminates at first and second ridges 1001, 1002, respectively. The third internal surface 712 is defined by and terminates at the second ridge 1002 and a third ridge 1003. The third ridge 1003 is configured to physically contact and mechanically obstruct corner b (or more generally, a respective corner 104) of the housing 100 when the ring 200 is rotated to the right (or more generally in a first direction) and/or when the housing 100 is rotated to the left (or more generally in a second direction). In the illustrated embodiment, the third ridge 1003 forces corner b to stay at or near the third rotational position relative to the ring 200 (e.g., at or near the third internal surface 712).

When corner b is aligned with the second ridge 1002, the gap between corner b and the second ridge 1002 is smaller than the gap between corner b and the third internal surface 712 (gap 910 in FIG. 9B) and the gap between corner b and the second internal surface 612 (gap 900 in FIG. 9A) to restrict or prevent relative rotation between the housing 100 and the ring 200. For example, when the ring 200 is in the third rotational position, the second and third ridges 1002, 1003 restrict or prevent relative rotation between the housing 100 and the ring 200.

When corner b is aligned with the first ridge 1001, the gap between corner b and the first ridge 1001 is smaller than the gap between corner b and the second internal surface 612 (gap 900 in FIG. 9A) to restrict or prevent relative rotation between the housing 100 and the ring 200. For example, when the ring 200 is in the second rotational position, the first and second ridges 1001, 1002 restrict or prevent relative rotation between the housing 100 and the ring 200.

It is noted that corner b can rotate across the first and second ridges 1001, 1002, but additional rotation force is needed to rotate corner b across the first and second ridges 1001, 1002 due to the smaller gap between corner b and the first and second ridges 1001, 1002, respectively.

Figure 10B:
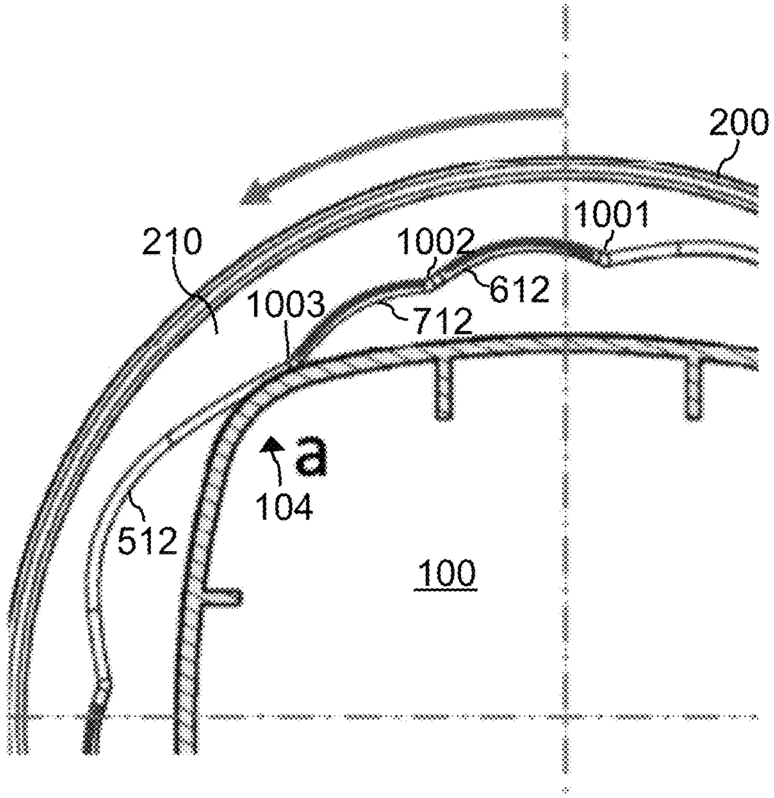
FIG. 10B is an enlarged view of the upper-left corner of the housing and a corresponding portion of the ring.

FIG. 10B is an enlarged view of the upper-left corner 104 of the housing 100 and a corresponding portion of the ring 200. The upper-left corner 104 corresponds to corner "a" in FIG. 7.

In the illustrated embodiment, the third ridge 1003 prevents the ring 200 from transitioning from the first rotational position, where corner a is aligned with the first internal surface 512, directly to the third the rotational position, where a is aligned with the third internal surface 712. For example, the third ridge 1003 is configured to physically contact and mechanically obstruct corner a (or more generally, a respective corner 104) of the housing 100 when the ring 200 is in the first rotational position relative to the housing 100 and the ring 200 is rotated to the left (or more generally in a second direction) and/or when the housing 100 is rotated to the right (or more generally in a first direction). Thus, the third ridge 1003 causes the housing 100 and the ring 200 to be rotationally configured in only one direction.

Figure 11:
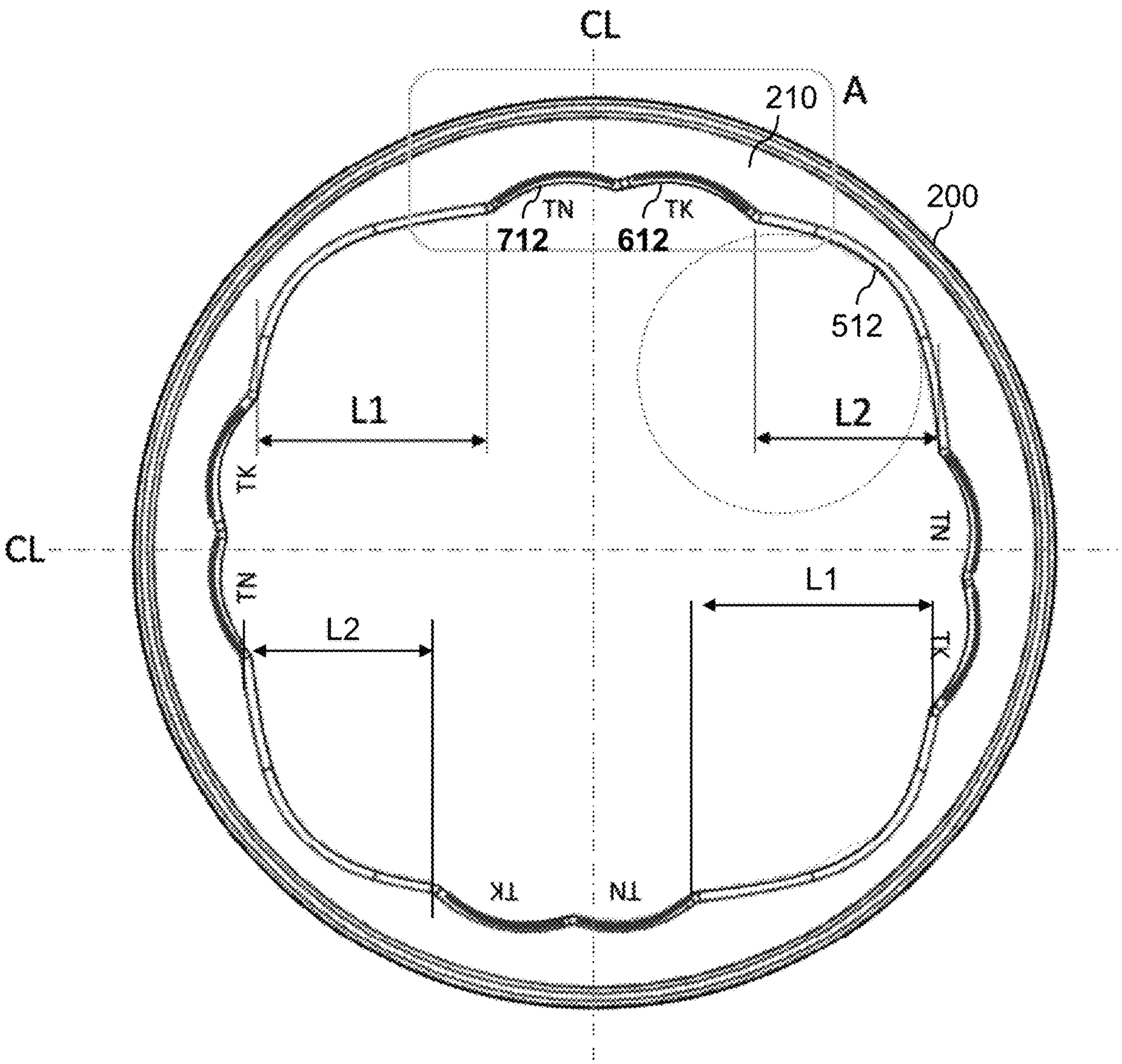
FIG. 11 is a bottom view of the ring according to an embodiment.

FIG. 11 is a bottom view of the ring 200 according to an embodiment. This view illustrates that the second and third internal surfaces 612, 712 can be off-center (e.g., rotationally- and/or angularly-offset) with respect to the first internal surfaces 512, which are centered in this view with respect to center lines (CLs). An angular offset of the second and third internal surfaces 612, 712 can be achieved by defining the first internal surfaces 512 on the upper-left-hand side and the lower-right-hand side of the ring 200 as having a length L1 with respect to the horizontal CL and by defining the first internal surfaces 512 on the upper-right-hand side and the lower-left-hand side of the ring 200 as having a length L2 with respect to the horizontal CL. L1 can be larger than L2 to provide the angular offset. The first internal surfaces 512 having lengths L1 and L2 have mirror-image symmetry in the ring 200. For example, the first internal surface 512 having lengths L1 can be located about 180 degrees from each other in the ring 200. Likewise, the first internal surface

512 having lengths L2 can be located about 180 degrees from each other in the ring 200.

In other embodiments, the first internal surfaces 512 can have the same length with respect to the horizontal CL. The first internal surfaces 512 can be symmetric in the ring 200 with respect to the vertical and/or the horizontal CLs.

Figure 12:
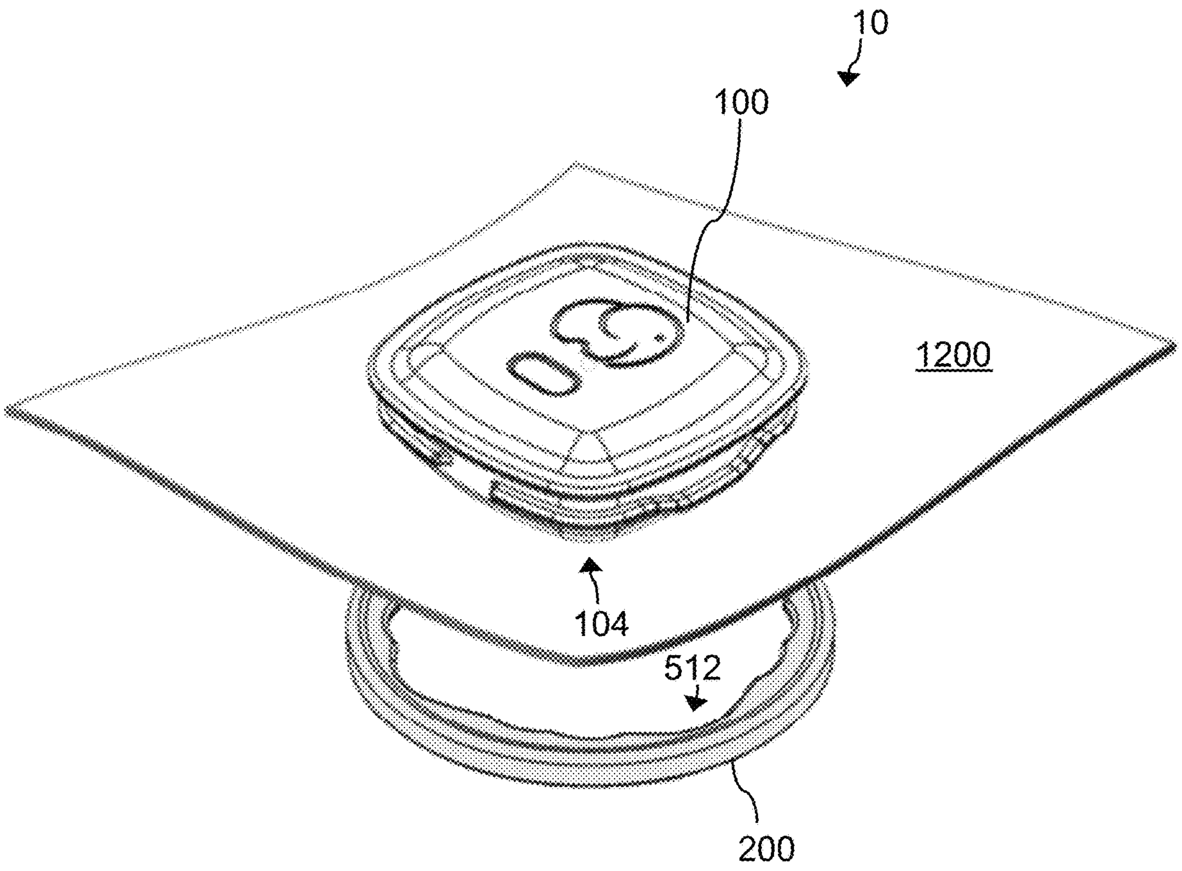
FIG. 12 is a perspective view of the apparatus to illustrate a first step in securing the apparatus to a flexible material such as an article of clothing.

FIG. 12 is a perspective view of the apparatus 10 to illustrate a first step in securing the apparatus to a flexible material 1200 such as an article of clothing. In this step, the apparatus 10 is in the unassembled configuration with the flexible material 1200 located between the housing 100 and the ring 200. The corners 104 of the housing 100 are preferably aligned with the first internal surfaces 512 in the ring 200 in this step. Aligning the corners 104 with the first internal surfaces 512 allows the housing 100 to be inserted into the ring 200 (or vice versa) to transition the apparatus 10 to the releasable configuration (e.g., as illustrated in FIG. 1).

Figure 13A:
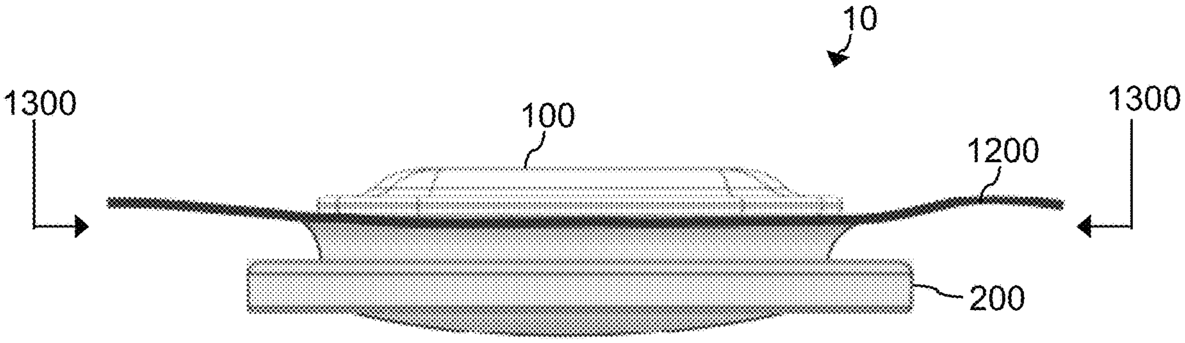
FIG. 13A is a side view of the apparatus to illustrate a second step in securing the apparatus to a flexible material.

FIG. 13A is a side view of the apparatus 10 to illustrate a second step in securing the apparatus to the flexible material 1200. In this step, the housing 100 is inserted into the ring 200 (or vice versa, i.e., the ring 200 is placed over the housing 100) to transition the apparatus 10 to the releasable configuration and the first rotational position in which the corners 104 are aligned with the first internal surfaces 512 (e.g., as illustrated in FIGS. 1 and 5).

Figure 13B:
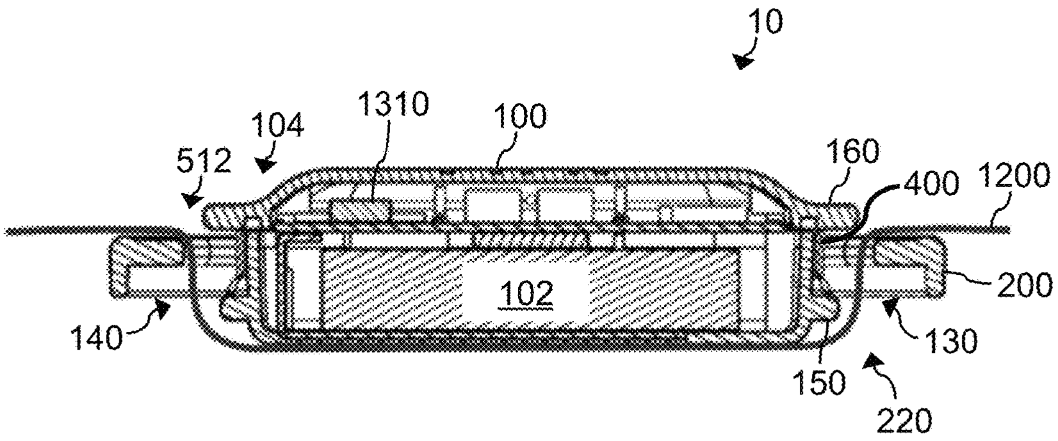
FIG. 13B is a cross section through the apparatus illustrated in FIG. 13A.

FIG. 13B is a cross section through apparatus 10 by the plane defined by lines 1300 in FIG. 13A. This view illustrates that the flexible material 1200 passes through the hole 220 in the ring 200. As such, the flexible material 1200 extends from a first side (e.g., the front side) of the ring 200 to a second side (e.g., the back side) of the ring 200. The flexible material 1200 is located between the first internal surfaces 512 of the ring 200 and the corners 104. For example, the flexible material 1200 is located between the gasket 400 on the side 130 at the corners 104 of the housing 100 and the first internal surfaces 512 of the ring 200.

This cross section also illustrates the electronics device 102 in the housing 100. In some embodiments, the electronics device 102 can include and/or be electrically coupled to a magnetometer 1310.

Figure 14A:
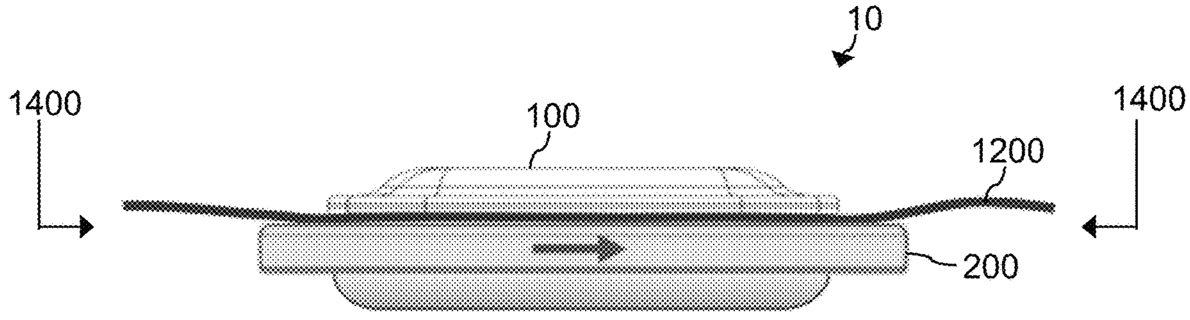
FIG. 14A is a side view of the apparatus to illustrate a third step in securing the apparatus to a flexible material.

FIG. 14A is a side view of the apparatus 10 to illustrate a third step in securing the apparatus to the flexible material 1200. In this step, the ring 200 is rotated counterclockwise relative to the housing 100 (or vice versa, i.e., the housing 100 is rotated clockwise relative to the ring 200) to transition the apparatus 10 to a locked configuration.

Figure 14B:
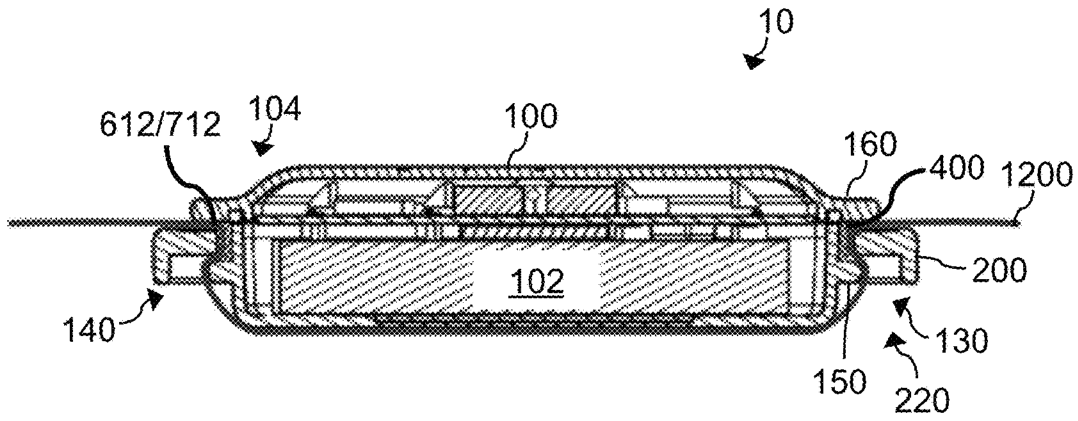
FIG. 14B is a cross section through the apparatus illustrated in FIG. 14A.

FIG. 14B is a cross section through apparatus 10 by the plane defined by lines 1400 in FIG. 14A.

In a first locked configuration, the corners 104 of the housing 100 are aligned with the second internal surfaces 612 (e.g., as illustrated in FIGS. 6 and 9A) in the second rotational position of the ring 200 relative to the housing 100. In this configuration, the flexible material 1200 is relatively thick and fills the gap 900 (FIG. 9A) between the gasket 400 and the second internal surfaces 612 at each corner 104 to form a friction-fit or press-fit lock. The gasket 400 can be partially or fully compressed depending on the thickness and the elasticity of the flexible material 1200.

In a second locked configuration, the corners 104 of the housing 100 are aligned with the third internal surfaces 712 (e.g., as illustrated in FIGS. 6 and 9B) in the third rotational position of the ring 200 relative to the housing 100. In this configuration, the flexible material 1200 is relatively thin and fills the gap 910 (FIG. 9B) between the gasket 400 and the third internal surfaces 712 at each corner 104 to form a friction-fit or press-fit lock. The gasket 400 can be partially or fully compressed depending on the thickness and the elasticity of the flexible material 1200.

Figure 15:
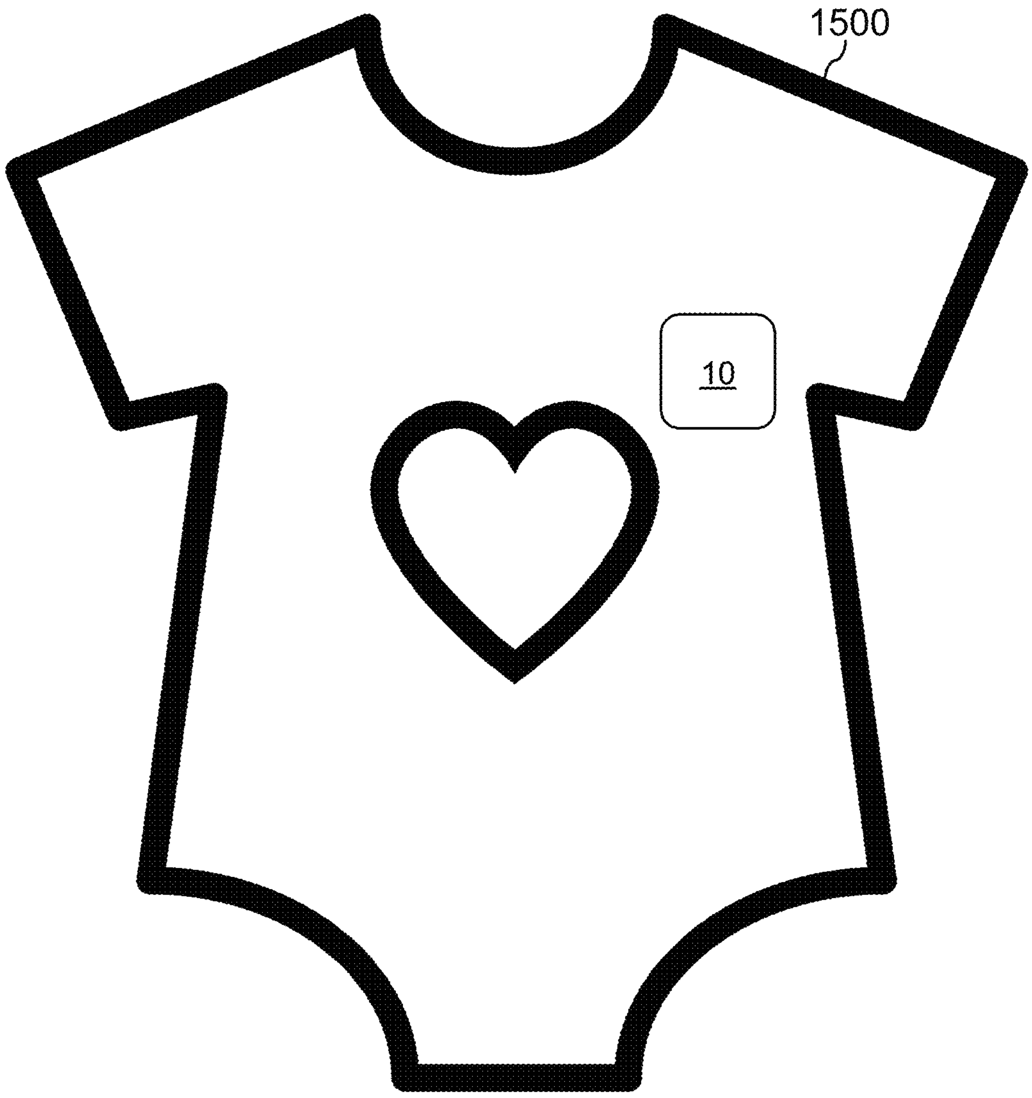
FIG. 15 illustrates an example of the apparatus attached to an article of baby clothing.

FIG. 15 illustrates an example of the apparatus 10 attached to an article of baby clothing 1500. The flexible material 1200 can be the same as or can include baby clothing 1500. The apparatus 10 is in a locked state.

Figure 16A:
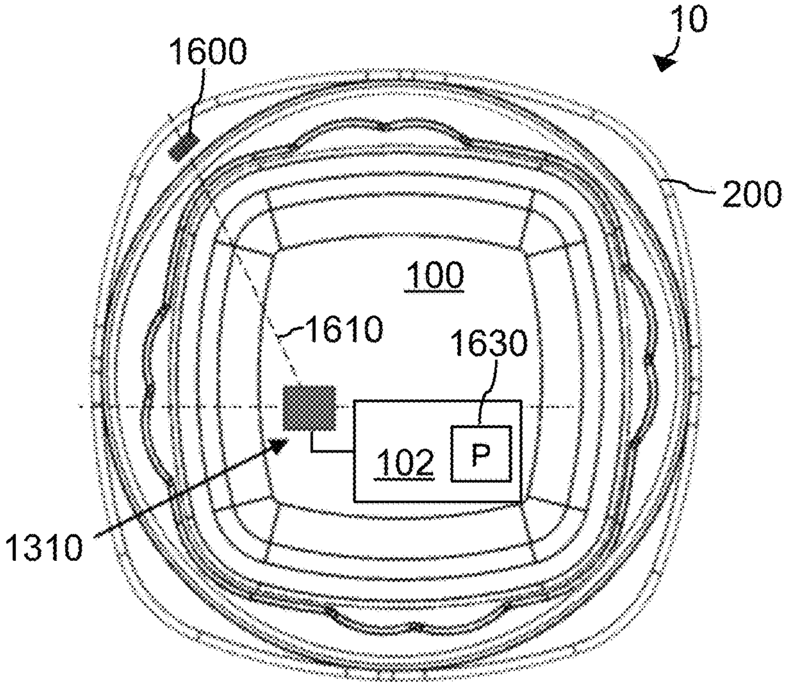
FIGS. 16A and 16B are top views of the apparatus according to another embodiment.
Figure 16B:
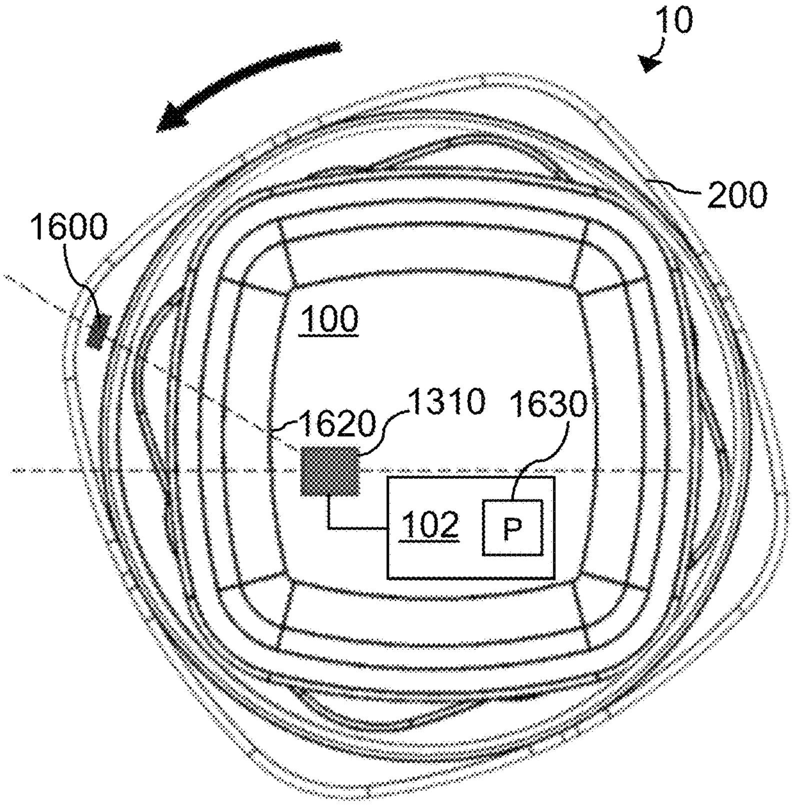

FIGS. 16A and 16B are side views of the apparatus 10 according to another embodiment. In this embodiment, a permanent magnet 1600 is located on or in the ring 200. The magnetic field produced by the permanent magnet 1600 can be measured by the magnetometer 1310 in the housing 100. The relative locations of the permanent magnet 1600 and the magnetometer 1310 are configured such that the magnitude of the magnetic field measured by at the direction of the magnetometer 1310 is different when the apparatus 10 is in the releasable configuration compared to when the apparatus 10 is in a locked position (e.g., the first or second locked configuration).

In FIG. 16A, the apparatus 10 is in the releasable configuration and the magnetometer 1310 is located a first location/position 1610 from the permanent magnet 1600 such that the magnetometer 1310 measures a first magnetic field.

In FIG. 16B, the apparatus 10 is in a locked position (e.g., the first or second locked configuration) and the magnetometer 1310 is located a second location/position 1620 from the permanent magnet 1600 such that the magnetometer 1310 measures a second magnetic field. Since the first location/position 1610 is different than the second location/position 1620, the first magnetic field measured by the magnetometer 1310 is different than the second magnetic field magnitude by the magnetometer 1310. For example, the first magnetic field can have a different magnitude and/or magnetic-field direction compared to the second magnetic field. The different magnetic-field directions can allow the first and second magnetic fields to be differentiated. Additionally or alternatively, the first and second magnetic fields can have different planes of movement, as sensed or measured by the magnetometer 1310.

The electronics device 102 can include a processor circuit 1630 that can be programmed to detect when one or more characteristics of the magnetic field measured by the magnetometer 1310 change (e.g., as a function of time) and indicate or represent that the apparatus 10 is in an unlocked state. The characteristics can include the magnitude, direction, and/or plane of movement of the magnetic field. For example, the processor circuit 1630 can be programmed to detect when the measured magnetic field magnitude falls below a predetermined threshold magnetic field magnitude, which can indicate that the apparatus 10 is in an unlocked state. The processor circuit 1630 can produce an output signal (e.g., a warning or alert signal) when the characteristic(s) of the magnetic field indicate or represent that the apparatus 10 is in an unlocked state.

Figure 17A:
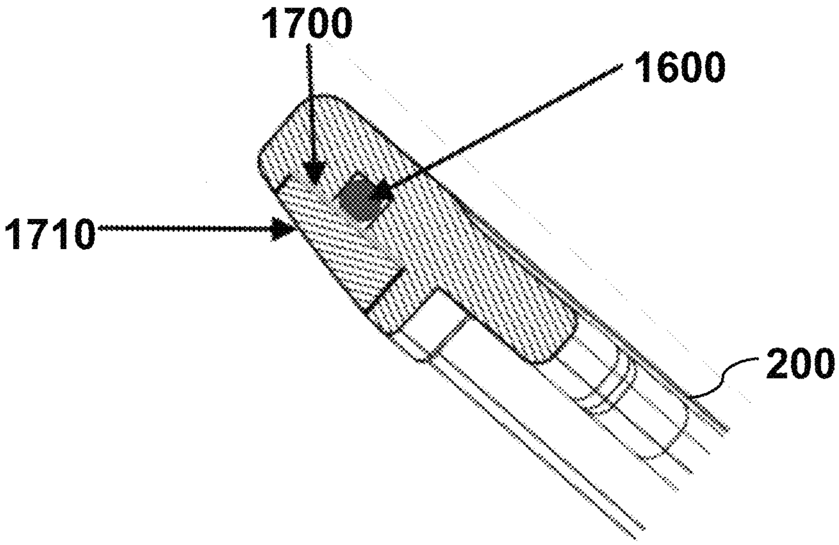
FIGS. 17A and 17B illustrate methods of attaching a permanent magnet to the inside of the ring.
Figure 17B:
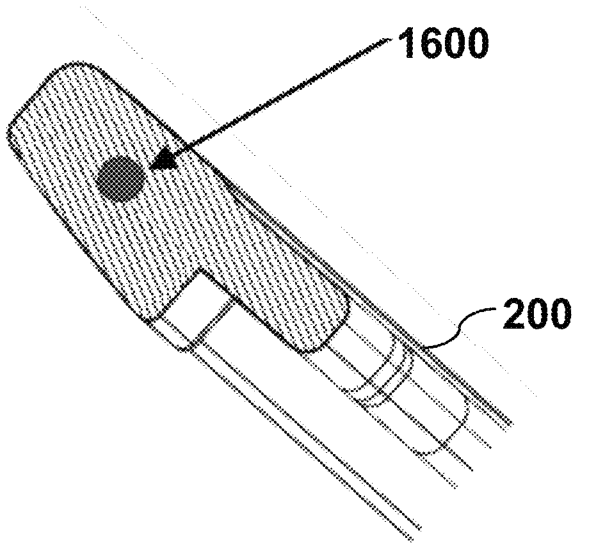

In one example, the permanent magnet 1600 is located in a cavity 1700 defined in the ring 200 that can be sealed with a cover 1710 (e.g., using glue and/or pins), as illustrated in FIG. 17A. In another example, the permanent magnet 1600 is attached to the inside of the ring 200 by over molding, as illustrated in FIG. 17B.

The invention should not be considered limited to the particular embodiments described above. Various modifications, equivalent processes, as well as numerous structures to which the invention may be applicable, will be readily apparent to those skilled in the art to which the invention is directed upon review of this disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of this application need not reside on a single computer or processor but may be distributed in a modular fashion among a number of different computers or processors to implement various aspects of this application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the disclosure and claims include new and novel improvements to existing methods and technologies, which were not previously known nor implemented to achieve the useful results described above. Users of the method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. An apparatus comprising:

a housing having a front, a back, and a side, the side having a slot that extends long a perimeter of the housing, the housing having a plurality of corners; and a ring having a variable-width wall along a circumference of the ring, the variable-width wall measured with respect to a radius of the ring, the variable-width wall defining multiple sets of internal surfaces, each set of internal surfaces configured to be aligned with the corners of the housing at different rotational positions of the ring relative to the housing, each set of internal surfaces defined by a respective width of the variable-width wall to define a respective gap between each corner of the housing and a respective set of internal surfaces when the corners are aligned with the respective set of internal surfaces, wherein when a thick flexible material is located between the housing and the ring, the apparatus is configured to form a first press-fit lock when the ring is rotated relative to the housing to attach the apparatus to the thick flexible material, wherein:

the plurality of internal surfaces includes a first set of internal surfaces configured to define a first opening in the ring, the first opening larger than a bottom of the housing to allow the housing to be placed within or removed from the ring when the ring is in a first rotational position relative to the housing, the first opening including a first gap between each corner of the housing and the first set of internal surfaces when the ring is in the first rotational position, the plurality of internal surfaces includes a second set of internal surfaces configured to define a second opening in the ring, the second opening including a second gap between each corner of the housing and the second set of internal surfaces when the ring is in a second rotational position relative to the housing, the second gap smaller than the first gap, wherein the apparatus is configured to transition to a first locked state when the thick flexible material is located between the housing and the ring including in the second gap to form the first press-fit lock, and the plurality of internal surfaces includes a third set of internal surfaces configured to define a third opening in the ring, the third opening including a third gap between each corner of the housing and the third set of internal surfaces when the ring is in a third rotational position relative to the housing, the third gap smaller than the second gap, wherein the apparatus is configured to transition to a second locked state when a thin flexible material is located between the housing and the ring including in the third gap to form a second press-fit lock, the thin flexible material being thinner than the thick flexible material.

2. The apparatus of claim 1, wherein the ring includes a flange along a circumference of the ring.

3. The apparatus of claim 1, wherein a gasket is located on the side of the housing, the gasket configured to compress when the apparatus is in the first locked state and/or in the second locked state to increase a range of thicknesses of the thick flexible material and/or of the thin flexible material, respectively, that can form the first press-fit lock and/or the second press-fit lock, respectively.

4. The apparatus of claim 3, wherein the gasket is located in a slot defined by first and second flanges, the first and second flanges overhanging the second and third internal surfaces when the ring is in the second and third rotational positions, respectively, relative to the housing, the first and second flanges restricting a movement of the housing relative to the ring in a direction orthogonal to a plane of the ring.

5. The apparatus of claim 4, wherein the first flange is larger than the first opening of the ring to mechanically engage the variable-width wall when the ring is in the first rotational position relative to the housing.

6. The apparatus of claim 1, wherein:

the housing has rounded corners, and each set of internal surfaces is rounded to conform to the rounded corners of the housing.

7. The apparatus of claim 6, wherein each of the third set of internal surfaces is at least partially defined by a respective ridge that is configured to physically contact the respective corner of the housing to prevent the ring from being rotated in a first direction beyond the third rotational position.

8. The apparatus of claim 7, wherein when the ring is in the first rotational position, the respective ridge is configured to physically contact the respective corner of the housing when the ring is rotated in a second direction, opposite to the first direction, such that the ring can only be rotated in the first direction to transition to the second and third rotational positions.

9. The apparatus of claim 6, wherein:

the respective ridge is a first respective ridge, and each of the third set of internal surfaces is at least partially defined by a respective second ridge that is configured to form a respective second-ridge gap between each corner of the housing and the respective second ridge when each corner is aligned with the respective second ridge, the respective second-ridge gap smaller than the second and third gaps to limit a relative rotation between the ring and the housing when the ring is in the second or third rotational position.

10. The apparatus of claim 9, wherein each of the second set of internal surfaces is at least partially defined by the respective second ridge and a respective third ridge, the respective third ridge configured to form a respective third-ridge gap between each corner of the housing and the respective third ridge when each corner is aligned with the respective third ridge, the respective third-ridge gap smaller than the second gap to limit the relative rotation between the ring and the housing when the ring is in the second rotational position.

11. The apparatus of claim 1, wherein:

the front and back of the housing have four corners, each set of internal surfaces has four internal interfaces, and when the ring is oriented such that the first set of internal surfaces is symmetric with respect to a center line of the ring, the second and third sets of internal surfaces are angularly offset with respect to the center line.

12. The apparatus of claim 11, wherein:

a first internal surface in the first set of internal surfaces is defined by a first length that is measured with respect to the center line, a second internal surface in the first set of internal surfaces is defined by a second length that is measured with respect to the center line, the first length is larger than the second length, and the first set of internal surfaces has a mirror-image symmetry in the ring.

13. An apparatus comprising:

a housing having a front, a back, and a side, the side having a slot that extends long a perimeter of the housing, the housing having a plurality of corners;

one or more electronic devices located in the housing; and a ring having a variable-width wall along a circumference of the ring, the variable-width wall measured with respect to a radius of the ring, the variable-width wall defining multiple sets of internal surfaces, each set of internal surfaces configured to be aligned with the corners of the housing at different rotational positions of the ring relative to the housing, each set of internal surfaces defined by a respective width of the variable-width wall to define a respective gap between each corner of the housing and a respective set of internal surfaces when the corners are aligned with the respective set of internal surfaces, wherein when a thick flexible material is located between the housing and the ring, the apparatus is configured to form a first press-fit lock when the ring is rotated relative to the housing to attach the apparatus to the thick flexible material, wherein:

the plurality of internal surfaces includes a first set of internal surfaces configured to define a first opening in the ring, the first opening larger than a bottom of the housing to allow the housing to be placed within or removed from the ring when the ring is in a first rotational position relative to the housing, the first opening including a first gap between each corner of the housing and the first set of internal surfaces when the ring is in the first rotational position, the plurality of internal surfaces includes a second set of internal surfaces configured to define a second opening in the ring, the second opening including a second gap between each corner of the housing and the second set of internal surfaces when the ring is in a second rotational position relative to the housing, the second gap smaller than the first gap, wherein the apparatus is configured to transition to a first locked state when the thick flexible material is located between the housing and the ring including in the second gap to form the first press-fit lock, and the plurality of internal surfaces includes a third set of internal surfaces configured to define a third opening in the ring, the third opening including a third gap between each corner of the housing and the third set of internal surfaces when the ring is in a third rotational position relative to the housing, the third gap smaller than the second gap, wherein the apparatus is configured to transition to a second locked state when a thin flexible material is located between the housing and the ring including in the third gap to form a second press-fit lock, the thin flexible material being thinner than the thick flexible material.

14. The apparatus of claim 13, wherein:

a permanent magnet is attached to or embedded in the ring;

the one or more electronic devices includes a magnetometer and a processor circuit in electrical communication with the magnetometer, the magnetometer measures a magnetic field produced by the permanent magnet, the magnetometer and the permanent magnet are positioned such that a relative position of the magnetometer with respect to the permanent magnet changes when the ring is in the second or third rotational position compared to when the ring is in the first rotational position, one or more characteristics of the magnetic field measured by the magnetometer is different when the ring is in the second or third rotational position compared to when the ring is in the first rotational position, and the processor circuit is configured to produce an output signal when the one or more characteristics of the magnetic field indicate(s) that the ring is in the first rotational position.

* * * * *